US00PP37160P2

(12) United States Plant Patent
van Langen

(10) Patent No.: US PP37,160 P2
(45) Date of Patent: Dec. 16, 2025

(54) ***ALOE* PLANT NAMED 'AMIAL2202'**

(50) Latin Name: *Aloe*
Varietal Denomination: AMIAL2202

(71) Applicant: NovoAmi B.V., Heerhugowaard (NL)

(72) Inventor: Gerard van Langen, Heerhugowaard (NL)

(73) Assignee: Novo Ami B.V., Heerhugowaard (NL)

( * ) Notice: Subject to any disclaimer, the term of this patent is extended or adjusted under 35 U.S.C. 154(b) by 0 days.

(21) Appl. No.: 18/831,364

(22) Filed: Dec. 12, 2024

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12; A01H 5/00
See application file for complete search history.

*Primary Examiner* — Kent L Bell
(74) *Attorney, Agent, or Firm* — Samuel R McCoy, Jr.

(57) ABSTRACT

A new and distinct *Aloe* plant named 'AMIAL2202' which is characterized by a rosette of succulent foliage that gives rise to an abundance of small, secondary rosettes which will eventually ring the entire primary rosette, foliage with an upright attitude, dark green foliage with a moderate abundance of light greyed-green, appearing nearly white, oblong protuberances loosely arranged in highly irregular transverse rows on the lower leaf surface, serrate leaf margins with an abundance of spine-like teeth, and the stability of these characteristics from generation to generation.

3 Drawing Sheets

Latin name of the genus and species: The Latin name of the genus and species of the novel variety disclosed herein is *Aloe* hybrid.

Variety denomination: The inventive variety of *Aloe* disclosed herein has been given the variety denomination 'AMIAL2202'.

BACKGROUND OF THE INVENTION

Parentage: 'AMIAL2202' is a seedling selection resulting from the controlled cross-pollination of an *Aloe arborescens* x *humilis* hybrid plant named 'AMIAL2135' (Community Plant Variety Rights No. 2021/1788) and an unnamed *Aloe vera* plant that typifies the species (not patented). The crossing was made by the inventor in the spring of 2020 at a commercial greenhouse in Heerhugowaard, the Netherlands. In the spring of 2021, one seedling was observed which exhibited an abundance of erect, dark green foliage with an abundance of oblong near-white protuberances and prominent dentate margins, unlike the parent plants and all other progeny in the trials. Upon confirmation of distinctness and stability, 'AMIAL2202' was selected for commercialization.

Asexual Reproduction: Asexual reproduction of the new cultivar 'AMIAL2202', by way of rooting leaf cuttings, was first initiated in the spring of 2022 at the inventor's commercial greenhouse in Heerhugowaard, the Netherlands. Through five subsequent generations, the unique features of this cultivar have proven to be stable and true to type.

SUMMARY OF THE INVENTION

The cultivar 'AMIAL2202' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIAL2202'. These characteristics in combination distinguish 'AMIAL2202' as a new and distinct *Aloe* hybrid plant:

1. 'AMIAL2202' exhibits a primary rosette of succulent foliage which gives rise to an abundance of small, secondary rosettes which will eventually ring the entire primary rosette with age; and
2. 'AMIAL2202' exhibits dark green succulent foliage which is held upright and slightly outward; and
3. 'AMIAL2202' exhibits dentate leaf margins with an abundance of large, spine-like teeth that are colored light greyed-green; and
4. 'AMIAL2202' exhibits a moderate abundance of light greyed-green, appearing nearly white, oblong protuberances loosely arranged in highly irregular transverse rows on the lower leaf surface.

BOTANICAL DESCRIPTION OF THE PLANT

Figure 1:
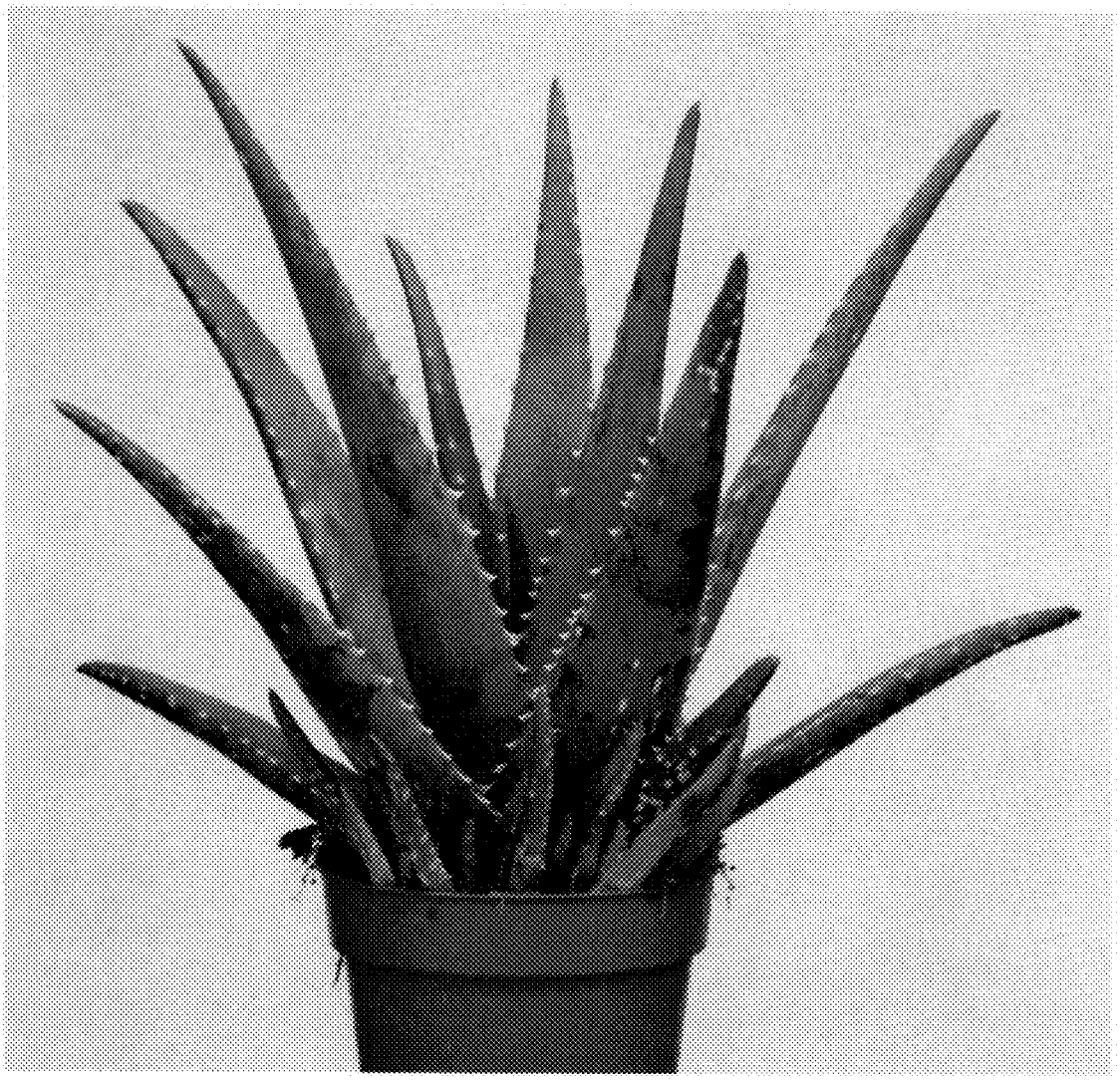
FIG. 1 illustrates, as nearly true as it is reasonably possible to make the same in color photographs of this type, an exemplary plant of 'AMIAL2202' grown in a commercial greenhouse in Honselersdijk, the Netherlands. This plant is approximately 30 weeks old, shown planted in a 12 cm container.
Figure 2:
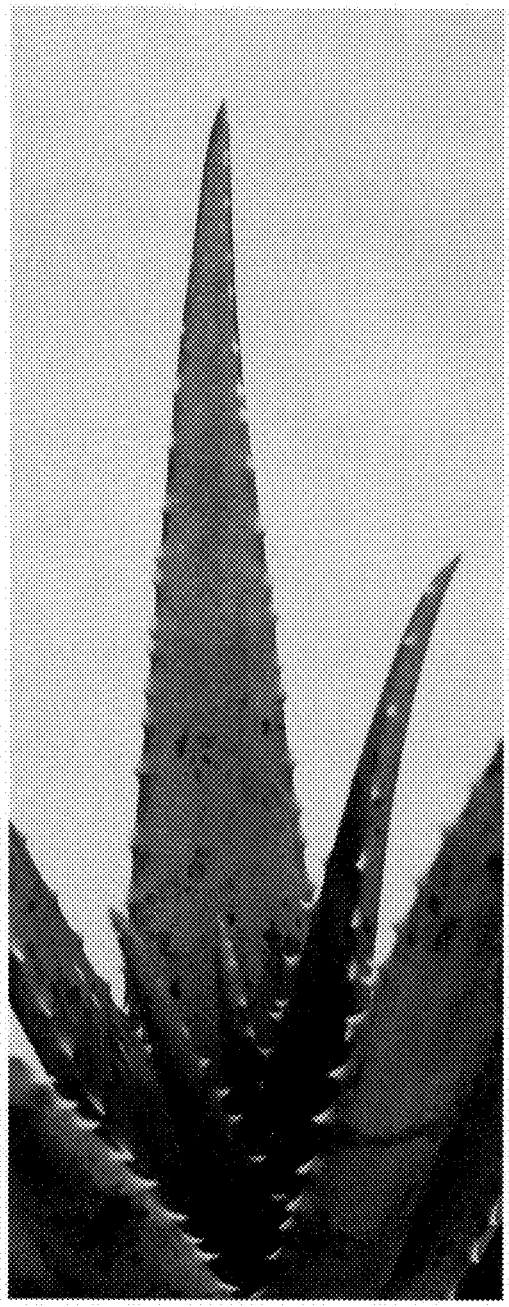
FIG. 2 illustrates, as nearly true as it is reasonably possible to make the same in color photographs of this type, adaxial surface of the mature foliage 'AMIAL2202'.
Figure 3:
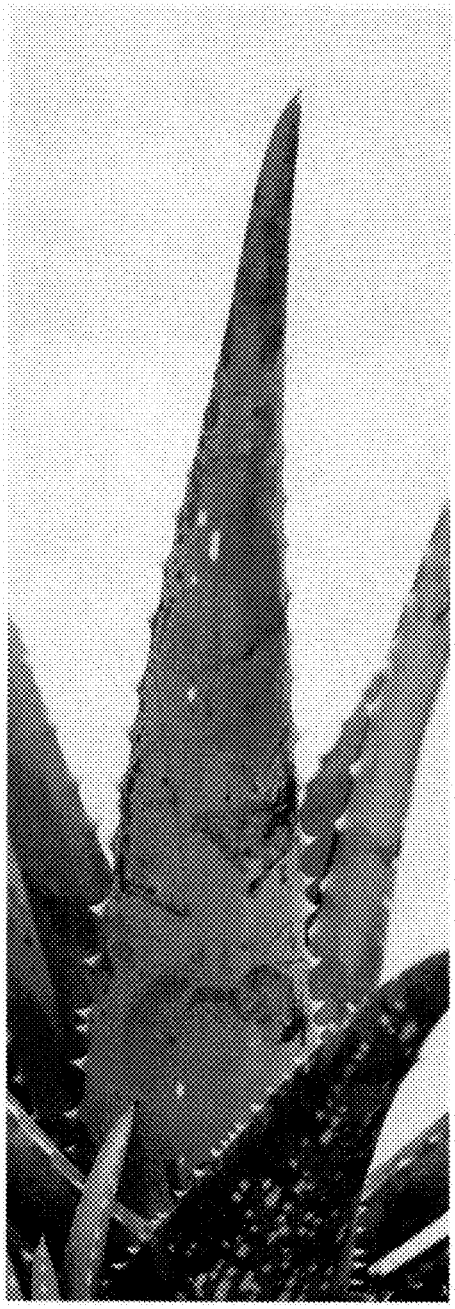
FIG. 3 illustrates, as nearly true as it is reasonably possible to make the same in color photographs of this type, the abaxial surface of the mature foliage of 'AMIAL2202'.

The following observations and measurements made in October of 2022 describe averages from a sample set of six specimens of 30-week-old 'AMIAL2202' plants grown in 12 cm nursery containers at commercial greenhouse in Honselersdijk, the Netherlands. Plants were produced using conventional greenhouse production protocols for *Aloe* which consisted of minimal overhead irrigation, minimal fertilizer applications, and control measures for common pests and diseases. Plants were produced under 50 percent shade and no photoperiodic treatments or artificial light was provided to the plants.

Those skilled in the art will appreciate that certain characteristics will vary with older or, conversely, with younger plants. 'AMIAL2202' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'AMIAL2202' and a comparison with the parent plants and the closest known commercial comparator is provided below.

Plant description:

*Growth habit*.—Succulent perennial with foliage growing in a basal rosette, eventually producing a short stem; secondary rosettes are eventually produced at the base, themselves eventually forming a short stem. Succulent perennial with foliage growing in a basal rosette; secondary rosettes are eventually produced at the base of the plant; 6 secondary rosettes observed.

*Plant shape*.—Basal rosette.

*Height from soil level to top of foliar plane*.—24.1 cm.

*Plant spread*.—Average of 28.9 cm.

*Growth rate*.—Moderately to highly fast growing.

*Plant vigor*.—Highly vigorous.

*Propagation*.—Type — Leaf cuttings. Time to initiate rooting — Approximately 21 days at 18 degrees Celsius. Crop time — Approximately 35 weeks to produce a marketable plant in a 12 cm container.

*Disease and pest resistance or susceptibility*.—Similar to other *Aloe* varieties.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Quantity*.—Singular.

*Cross-section*.—Terete.

*Length*.—2.4 cm.

*Diameter*.—5.6 cm.

*Texture*.—Smooth, slightly glossy.

*Color*.—Greyed-green, nearest to a blend of RHS N138B and 191A.

*Attitude*.—Vertical.

Foliage:

*Arrangement*.—Spiraled.

*Division*.—Simple.

*Attachment*.—Sessile.

*Quantity*.—Approximately 15 leaves per rosette.

*Shape*.—Lanceolate; succulent.

Dimensions.—21.6 cm long, 5.2 cm wide, and 1.1 cm thick, on average.

*Aspect*.—Flattened terete.

*Attitude*.—Flat to very slightly concave; leaf-bases are nearly horizontal, leaf blades curve upwards from the base at an average angle of 55-degrees with an apex that curves slightly downward at an average angle of 10-degrees to the leaf blade.

*Apex*.—Long and narrow acuminate.

*Base*.—Broad cuneate.

*Margin*.—Serrate; not undulated or lobed. Serrate spines have an average length of 0.3 cm and are colored light greyed-green, appearing nearly-white, nearest to RHS 192D.

*Texture, adaxial surface*.—Smooth, glabrous, and glaucous.

*Texture, abaxial surface*.—Glaucous, and moderately covered with oblong protuberances, each approximately 0.4 cm in length and 0.2 cm in diameter; spots are irregularly arranged in highly irregular transverse rows.

*Luster, adaxial surface*.—Slightly glossy, due to the epicuticular wax.

*Luster, abaxial surface*.—Slightly glossy, due to the epicuticular wax.

*Color*.—Juvenile foliage, adaxial surface — Green, nearest to RHS 137B; epicuticular wax is green to greyed-green, nearest to a blend of RHS N138B and 191A. Juvenile foliage, abaxial surface — Green, nearest to RHS 137C; epicuticular wax is green to greyed-green, nearest to a blend of RHS N138B and 191A. Mature foliage, adaxial surface — Green, nearest to RHS NN137B; epicuticular wax is green to greyed-green, nearest to a blend of RHS N138B and 191A. Mature foliage, abaxial surface — Green, nearest to RHS NN137B; epicuticular wax is green to greyed-green, nearest to a blend of RHS N138B and 191A and protuberances are greyed-green, nearest to RHS 193B. Venation — No venation visible.

Inflorescence: No flowering has been observed to date.

COMPARISONS WITH THE PARENT PLANT

Plants of the new cultivar 'AMIAL2202' differ from the seed parent, *Aloe* hybrid 'AMIAL2135' (Community Plant Variety Rights No. 2021/1788), in the following characteristics described in Table 1 below.

TABLE 1

| Characteristic | 'AMIAL2202' | The seed parent. |
|---|---|---|
| Foliage size. | Larger than the seed parent. | Smaller than 'AMIAL2202' |
| Foliage attitude. | More upright than the seed parent. | More relaxed than 'AMIAL2202'. |

Plants of the new cultivar 'AMIAL2202' differ from the pollen parent, an unnamed *Aloe vera* (not patented), in the following characteristics described in Table 2 below.

TABLE 2

| Characteristic | 'AMIAL2202' | The pollen parent. |
|---|---|---|
| General coloration of the foliage. | A darker shade of green, relative to the pollen parent. | A lighter shade of green, relative to 'AMIAL2202'. |
| Plant size. | Smaller than the pollen parent. | Larger than 'AMIAL2202'. |
| Size of foliar protuberances. | Smaller than the pollen parent. | Larger than 'AMIAL2202'. |
| Abundance of foliar protuberances. | Less abundant. | More abundant. |

COMPARISONS WITH THE CLOSEST KNOWN COMPARATOR

Plants of the new cultivar 'AMIAL2202' differ from *Aloe* hybrid 'AMIAL2136' (U.S. Plant Pat. No. 36,929), in the following characteristics described in Table 3 below.

TABLE 3

| Characteristic | 'AMIAL2202' | 'AMIAL2136' |
|---|---|---|
| Foliage attitude. | Flat to very slightly concave in a basal arrangement; leaf-bases are nearly horizontal. Leaf blades curve upwards from the base at an average angle of 55-degrees with an apex that curves slightly downward at an average angle of 10-degrees to the leaf blade. | Upward with a slight bend outward in a basal arrangement at an approximate angle of 50 degrees, growing at a varying angle between 30 to 70 degrees distally from the base with leaf apices that are curved slightly downward at an average angle of 30 degrees to the leaf blade. |
| Presence of foliar protuberances. | The abaxial surface of the mature foliage are moderately covered with spots irregularly arranged in highly irregular transverse rows. | The abaxial surface of the oldest are sparsely to moderately covered with small orbicular protuberances arranged in irregular longitudinal rows. |
| Foliage size. | Smaller than 'AMIAL2136'. | Larger than 'AMIAL2202'. |
| General coloration of the foliage. | Lighter green to greyed-green than 'AMIAL2136'. | Darker green than 'AMIAL2202'. |

That which is claimed is:

1. A new and distinct variety of *Aloe* plant named 'AMIAL2202', substantially as described and illustrated herein.

* * * * *